(12) United States Patent
Washburn et al.

(10) Patent No.: US 9,500,944 B2
(45) Date of Patent: Nov. 22, 2016

(54) METHOD AND APPARATUS FOR CONTROLLING ULTRASOUND SYSTEMS WITH PHYSICAL CONTROLS

(75) Inventors: Michael Joseph Washburn, Brookfield, WI (US); David Dixon Voight, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 1523 days.

(21) Appl. No.: 11/713,764

(22) Filed: Mar. 2, 2007

(65) Prior Publication Data
US 2008/0215982 A1 Sep. 4, 2008

(51) Int. Cl.
| G06F 3/00 | (2006.01) |
| G06F 3/048 | (2013.01) |
| G03B 42/06 | (2006.01) |
| A61B 8/08 | (2006.01) |
| A61B 8/00 | (2006.01) |
| G01S 7/52 | (2006.01) |

(52) U.S. Cl.
CPC ............... *G03B 42/06* (2013.01); *A61B 8/08* (2013.01); *A61B 8/461* (2013.01); *A61B 8/467* (2013.01); *G01S 7/52084* (2013.01); *A61B 8/0866* (2013.01); *A61B 8/488* (2013.01)

(58) Field of Classification Search
CPC .................................. G06F 3/048; G06F 3/00
USPC ................... 715/773; 600/437, 400
See application file for complete search history.

(56) References Cited

U.S. PATENT DOCUMENTS

| 5,161,535 | A | 11/1992 | Short et al. |
| 5,844,140 | A | 12/1998 | Seale |
| 5,919,138 | A | 7/1999 | Ustuner |
| 5,934,288 | A * | 8/1999 | Avila et al. ............ 600/443 |
| 6,063,030 | A * | 5/2000 | Vara et al. ............ 600/437 |
| 6,394,575 | B1 | 5/2002 | Kent |
| 6,425,865 | B1 * | 7/2002 | Salcudean et al. .......... 600/437 |
| 6,464,642 | B1 | 10/2002 | Kawagishi |
| 6,503,205 | B2 | 1/2003 | Manor et al. |
| 6,636,197 | B1 * | 10/2003 | Goldenberg et al. ........ 345/156 |
| 6,872,178 | B2 | 3/2005 | Weinberg |
| 7,052,459 | B2 * | 5/2006 | Washburn et al. .......... 600/437 |
| 7,103,205 | B2 | 9/2006 | Wang et al. |
| 7,180,501 | B2 * | 2/2007 | Marvit et al. ............ 345/156 |
| 7,313,260 | B2 * | 12/2007 | Wang et al. ............ 382/128 |
| 7,365,735 | B2 * | 4/2008 | Reinhardt et al. ......... 345/156 |
| 7,463,241 | B2 * | 12/2008 | Ushimaru et al. ......... 345/161 |

(Continued)

FOREIGN PATENT DOCUMENTS

| EP | 0520338 A2 | 12/1992 |
| EP | 1228810 A2 | 8/2002 |

(Continued)

*Primary Examiner* — Amy Ng
*Assistant Examiner* — Erik Stitt
(74) *Attorney, Agent, or Firm* — Dean D. Small; The Small Patent Law Group, LLC

(57) ABSTRACT

A user interface for controlling an ultrasound system comprises a display for displaying ultrasound data and a plurality of physical controls. At least one of the physical controls is configured to control multiple functions of the ultrasound system and has a user operable member providing physical actions that are associated with system parameters. The physical actions comprise rotational and translational movements, and each of the system parameters is associated with an ultrasound system action.

23 Claims, 7 Drawing Sheets

(56) References Cited

U.S. PATENT DOCUMENTS

| | | | |
|---|---|---|---|
| 7,516,416 B2* | 4/2009 | Viswanathan et al. | 715/781 |
| 7,540,866 B2* | 6/2009 | Viswanathan et al. | 606/1 |
| 7,549,961 B1* | 6/2009 | Hwang | 600/440 |
| 2002/0042574 A1 | 4/2002 | Manor et al. | |
| 2002/0167549 A1* | 11/2002 | Cupples et al. | 345/835 |
| 2003/0019316 A1* | 1/2003 | Tews | 74/471 XY |
| 2003/0220564 A1* | 11/2003 | Wilkins et al. | 600/437 |
| 2004/0179332 A1* | 9/2004 | Smith et al. | 361/681 |
| 2004/0227725 A1* | 11/2004 | Calarco et al. | 345/156 |
| 2005/0054920 A1* | 3/2005 | Washburn et al. | 600/437 |
| 2005/0116935 A1* | 6/2005 | Washburn | 345/167 |
| 2005/0119528 A1 | 6/2005 | Weinberg | |
| 2005/0131700 A1* | 6/2005 | Washburn et al. | 704/270 |
| 2006/0025679 A1* | 2/2006 | Viswanathan et al. | 600/424 |
| 2006/0030775 A1* | 2/2006 | Adams et al. | 600/437 |
| 2006/0041181 A1* | 2/2006 | Viswanathan et al. | 600/11 |
| 2006/0202865 A1* | 9/2006 | Nguyen | 341/22 |
| 2006/0257009 A1* | 11/2006 | Wang et al. | 382/128 |
| 2007/0073148 A1* | 3/2007 | Kim | 600/437 |
| 2008/0146922 A1* | 6/2008 | Steins et al. | 600/437 |
| 2008/0221446 A1* | 9/2008 | Washburn et al. | 600/437 |

FOREIGN PATENT DOCUMENTS

| | | |
|---|---|---|
| EP | 1769390 A2 | 4/2007 |
| JP | 05-220142 A | 8/1993 |
| JP | 09-262208 A | 10/1997 |
| JP | 2001-128975 A | 5/2001 |
| JP | 2001-175890 A | 6/2001 |
| JP | 2001-283188 A | 10/2001 |
| JP | 2002-240268 A | 8/2002 |
| WO | WO 9515521 A2 | 6/1995 |
| WO | WO02091906 A2 | 11/2002 |
| WO | WO 03/101303 A1 | 12/2003 |
| WO | WO2005119505 A2 | 12/2005 |

* cited by examiner

METHOD AND APPARATUS FOR CONTROLLING ULTRASOUND SYSTEMS WITH PHYSICAL CONTROLS

BACKGROUND OF THE INVENTION

This invention relates generally to ultrasound systems, and more particularly, to methods and devices for controlling ultrasound systems with a user interface.

When imaging a patient with an ultrasound imaging device, the user typically holds the probe or transducer on the patient with one hand and controls the operation of the system with the other hand. For example, physical controls such as rotaries, toggles, pushbuttons, trackball, keyboard and the like may be placed on a surface of the system. It is desirable for a user to learn the location and function of the physical controls without having to look away from the ultrasound image on the display.

Some of the physical controls may be context sensitive, meaning that activating the physical control will result in a system response or action that is based on the state of the system. For example, a rotary control may adjust one system parameter during a heart scan and a different system parameter during a thyroid scan. In these cases, a context-sensitive label may be displayed near the control or on the main display to indicate the system parameter to the user. Mapping context sensitive physical controls may be provided to the user as an attempt to group functions close together and/or minimize the number of physical controls needed overall.

Unfortunately, it is often difficult to intuitively match the user's physical action with the desired system action or response. For example, if the physical control on the user interface is a rotary device and the system response is adjustment of the brightness on the display, many users would find it logical to turn the control clockwise (CW) to increase the brightness and counter-clockwise (CCW) to reduce the brightness. However, if the physical control is the rotary device and the system action is physically moving a parameter, such as the Doppler baseline, up and down on the display or left and right (such as for Doppler steering), users do not consistently move the physical control in the mapped CW/CCW direction to achieve the desired system response. Also, variation exists from one user to the next.

A variety of different context sensitive physical controls may be made available, such as up/down toggle switches, left/right toggle switches, rotary devices and pushbuttons. For example, if a user interface provides five context sensitive physical controls, two of the controls may be rotary devices, two of the controls may be up/down toggle switches, and one control may be a pushbutton. Alternatively, a rotary control may have the additional functionality of a pushbutton. Still, for a given machine state, the system actions to be performed may not match well to the available physical controls. For example, in one machine state, the use of five rotary devices may be the most intuitive for the five system actions that need to be controlled, leaving no physical room for toggle switches or pushbuttons, which may be the most intuitive physical actions to control system actions for a different machine state.

Additional buttons or controls may be positioned in combination to each other. For example, pushbuttons may be located proximate to a rotary device, such as one button above and one below, or one above, one below, one to the left and one to the right. Then, pushbuttons located above and below the rotary may be mapped to system actions requiring up/down motion. One disadvantage is that the physical action the user takes to move a parameter up and down on the display is mapped to two pushbuttons and may still not be intuitive to the user. Another disadvantage is that the multiple controls require significant space or must be made smaller than the ideal size in order to take up less space. Making the physical controls smaller and/or positioning the controls closer together makes the controls more difficult to use. Space is a particularly important factor in general for smaller ultrasound machines, such as ultrasound machines that are hand-carried or otherwise miniaturized. Therefore user interfaces that match the scale of the rest of the device and can provide desired functionality within the space constraints are desirable.

Thus, known physical controls on a user interface of an ultrasound system are not configured to perform intuitive actions and contextually based intuitive actions while minimizing the required physical space.

BRIEF DESCRIPTION OF THE INVENTION

In one embodiment, a user interface for controlling an ultrasound system comprises a display for displaying ultrasound data and a plurality of physical controls. At least one of the physical controls is configured to control multiple functions of the ultrasound system and has a user operable member providing physical actions that are associated with system parameters. The physical actions comprise rotational and translational movements, and each of the system parameters is associated with an ultrasound system action.

In another embodiment, a method for controlling an ultrasound system comprises detecting a first physical action of a multiple function (multi-function) control. The first physical action is a rotational movement, and a first system action associated with the first physical action is performed. A second physical action of the multi-function control is detected. The second physical action is a translational movement in one of first and second directions that are different with respect to each other. A second system action associated with the second physical action is performed. The first and second system actions are different with respect to each other.

In yet another embodiment, a method for controlling an ultrasound system comprises detecting a machine state of an ultrasound system. A physical action of a user control interconnected with the ultrasound system is detected. The physical action is one of at least four physical states of the user control. A system action associated with the physical action and the machine state is performed.

DETAILED DESCRIPTION OF THE INVENTION

Figure 1:
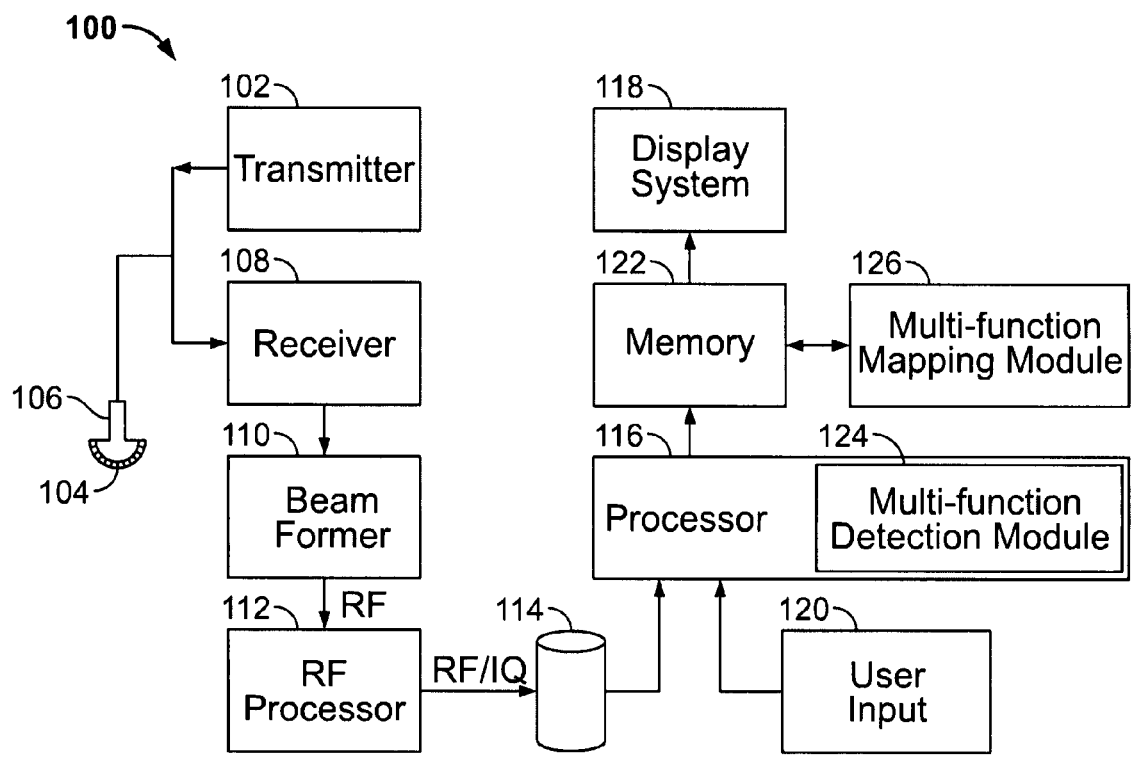
FIG. 1 illustrates a block diagram of an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 illustrates a block diagram of an ultrasound system 100. The ultrasound system 100 includes a transmitter 102 that drives transducers 104 within a probe 106 to emit pulsed ultrasonic signals into a body. A variety of geometries may be used. The ultrasonic signals are back-scattered from structures in the body, like blood cells or muscular tissue, to produce echoes that return to the transducers 104. The echoes are received by a receiver 108. The received echoes are passed through a beamformer 110 that performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage. A user input 120 as described in more detail below may be used to control operation of the ultrasound system 100, including, to control the input of patient data, to change a scanning or display parameter, and the like.

The ultrasound system 100 also includes a processor 116 to process the acquired ultrasound information (i.e., RF signal data or IQ data pairs) and prepare frames of ultrasound information for display on display system 118. The processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information may be displayed on the display system 118 at a slower frame-rate. A memory 122 is included for storing processed frames of acquired ultrasound information that are not scheduled to be displayed immediately. In an exemplary embodiment, the memory 122 is of sufficient capacity to store at least several seconds worth of frames of ultrasound information. The frames of ultrasound information are stored in a manner to facilitate retrieval thereof according to its order or time of acquisition. The memory 122 may comprise any known data storage medium.

A multiple function (multi-function) detection module 124 may be provided within the processor 116 and may be implemented in hardware or software, or a combination thereof. The multi-function detection module 124 receives signals from multi-function controls (as discussed below) provided on the user input 120. The multi-function controls may be activated through a user operable member, such as a knob and/or a multi-position joystick. The multi-function detection module 124 monitors the multi-function controls to identify if a physical action has occurred, such as translational or rotational movements or a push movement. An example of translational movement may be up/down, left/right or other directional toggle, while a rotational movement may be a rotation in the clockwise (CW) and/or counter-clockwise (CCW) directions. The multi-function detection module 124 also monitors the multi-function controls to identify whether the control is being maintained in a particular state, such as whether the control is being held in the up toggle position for a length of time exceeding a predetermined duration threshold. The multi-function detection module 124 also monitors the multi-function controls for speed of movement, such as whether the control is being rotated at a speed of rotation that exceeds a predetermined speed threshold. The predetermined duration threshold and the predetermined speed threshold may be stored in the memory 122, and are not determined by the particular multi-function control. The thresholds may also be determined by the system state or may be set or selected on and off by the user.

The multi-function detection module 124 transfers the information to a multi-function mapping module 126 that may optionally be stored within the processor 116. The multi-function mapping module 126 may be implemented in hardware or software, or a combination thereof. The multi-function mapping module 126 may store tables, charts, databases, and/or other mapping functionality to map particular system function(s) to a physical control. The mapping may change based on the state of the system 100 and/or protocol being used. The multi-function mapping module 126 uses the information to identify the system parameter or function to be modified. The multi-function mapping module 126 may also enact a rate of change to the system response based on the physical control being maintained in a particular position or state, or based on the rate of change detected by the multi-function detection module 124 with respect to the predetermined duration threshold and/or the predetermined speed threshold.

Figure 2:
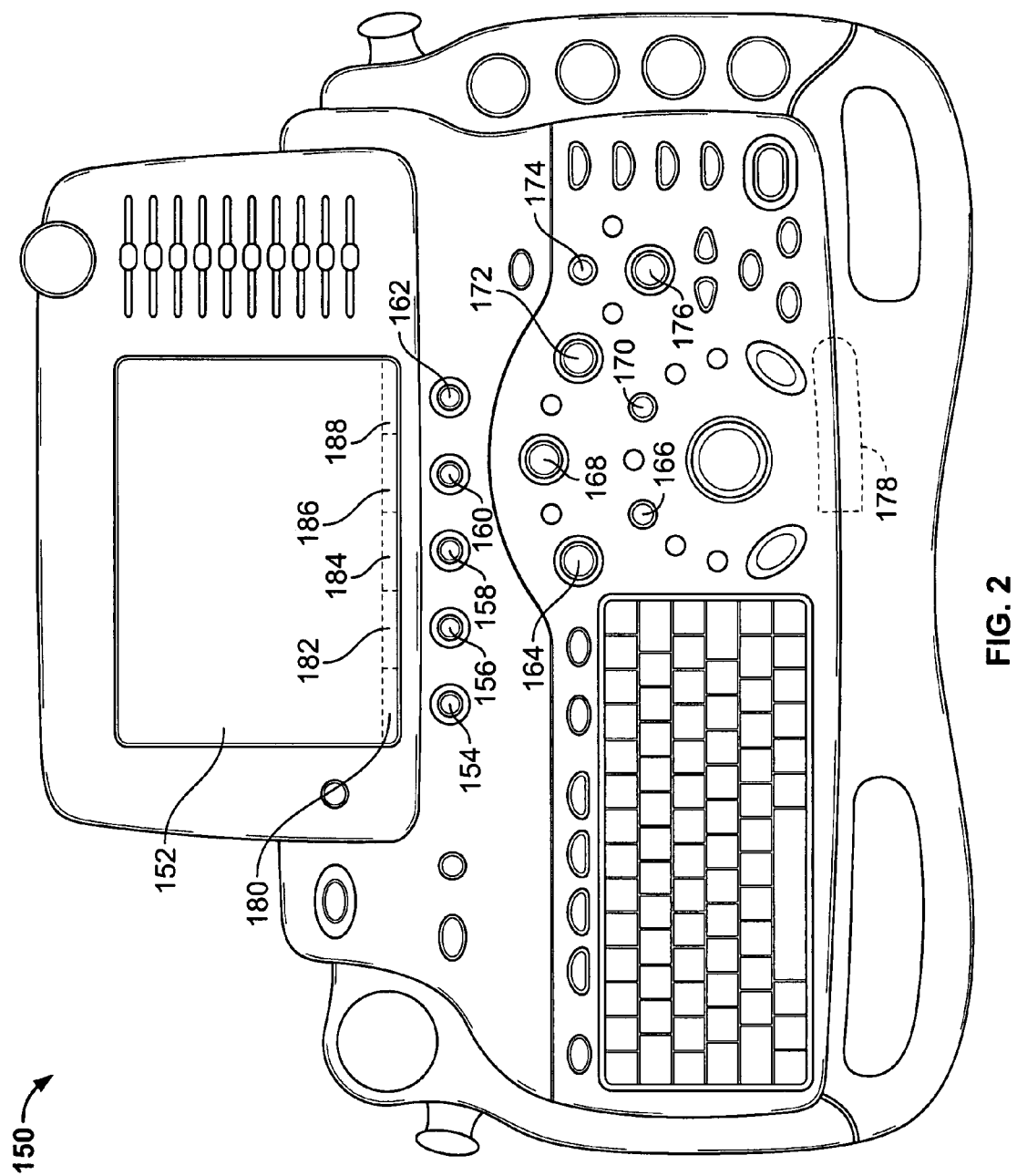
FIG. 2 illustrates a user interface formed in accordance with an embodiment of the present invention that may be used with the ultrasound system of FIG. 1.

FIG. 2 illustrates a user interface 150 that may be used with the ultrasound system 100 and the user input 120 shown in FIG. 1. The user interface 150 provides multiple interface options that the user may physically manipulate to interact with ultrasound data and other data that may be displayed, as well as to input information and set and change scanning parameters. The interface options may be used for specific inputs, programmable inputs, contextual inputs, and the like. Different types of physical controls are provided as different physical actions are more intuitive to the user for accomplishing specific system actions and thus achieving specific system responses. Some of the interface options generically illustrated on the user interface 150, such as a keyboard and trackball, will not be discussed herein.

A display 152 is also provided on the user interface 150. Although illustrated as integrated, it should be understood that the display 152 may be separate or separable from the user interface 150. The display 152 may optionally be a touchscreen, allowing the user to select options by touching displayed graphics, icons, and the like.

First, second, third, fourth and fifth multi-function controls 154, 156, 158, 160 and 162 are positioned proximate to the display 152. Each of the first through fifth multi-function controls 154-162 provides a plurality of different physical states. For example, a single multi-function control may provide movement functionality of a CW/CCW rotary, up/down toggle, left/right toggle, other positional toggle, and on/off or pushbutton, thus allowing a plurality of different states, such as eight or twelve different states. Different combinations are possible and are not limited to those discussed herein. Optionally, less than eight states may be provided, such as CW/CCW rotary functionality with at least two toggle positions, such as up/down toggle and/or left/right toggle. Optionally, at least two toggle positions may be provided with pushbutton functionality. The first through fifth multi-function controls 154-162 may be configured, for example, as joystick rotary controls.

The first, second, third, fourth and fifth multi-function controls 154-162 may be associated with labels displayed on the display 152 in first, second, third, fourth, and fifth label display areas 180, 182, 184, 186, and 188, respectively. Alternatively, a label may be displayed on a different display area such as an LED or other small display located proximate to an associated multi-function control.

Each of the first through fifth multi-function controls 154-162 may be context sensitive and thus context sensitive information may be displayed on the associated label. The label indicates a system parameter that is associated with and changed by a physical action of the multi-function control within the current context or system state. The system parameter is linked to a system action or response. The physical action may be predetermined, for example, based on one that is most logical to the user to accomplish the associated system action. If the multi-function control is context sensitive, the system parameters associated with the physical actions may change based on the ultrasound application and/or context or state of the ultrasound machine. For example, the associations may be different when acquiring a cardiac scan compared to a liver scan. Depending upon what machine state the ultrasound system 100 is in, one or more of the physical actions of the first through fifth multi-function controls 154-162 may be mapped to a different system parameter and/or may not be assigned or mapped to any system parameter.

Sixth, seventh, eighth, ninth, tenth, eleventh, and twelfth multi-function controls 164, 166, 168, 170, 172, 174 and 176 are provided on the user interface 150. It should be understood that more or less multi-function controls may be provided. One, some or all of the sixth through twelfth multi-function controls 164-176 may be context sensitive as discussed previously. Although not illustrated, one or more of the sixth through twelfth multi-function controls 164-176 may be associated with a label displayed on a display proximate to the particular multi-functional control.

Each of the first through twelfth multi-function controls 154-176 are configured to achieve multiple functions within the same physical space as a traditional rotary device, a rotary device that can be pushed, a pushbutton, or a toggle switch. Therefore, the number of functions that can be performed within a given area of space on the user interface 150 is increased. Also, the intuitive connection between the physical action required of the user and the system response is improved as more physical options are available.

With the use of a plurality of multi-function controls, the user interface 150 may be more intuitive for the user. Also, some controls may be removed as the more system functions may be performed by a single multi-function control. Therefore, the size of the user interface 150 may become smaller, and more functionality may be provided on ultrasound machines that are already small in size, such as a hand carried ultrasound scanner.

Although not limited to the arrangement as illustrated, the sixth through twelfth multi-function controls 164-176 may be arranged proximate one another such that the user may maintain the position of the user's hand without much movement. For example, a user's wrist may be positioned proximate to a wrist rest area 178. The user may then operate the sixth and seventh multi-function controls 164 and 166 with a first finger, the eighth and ninth multi-function controls 168 and 170 with a second finger, the tenth multi-function control 172 with a third finger, and the eleventh and twelfth multi-function controls 174 and 176 with a fourth finger.

Figure 3:
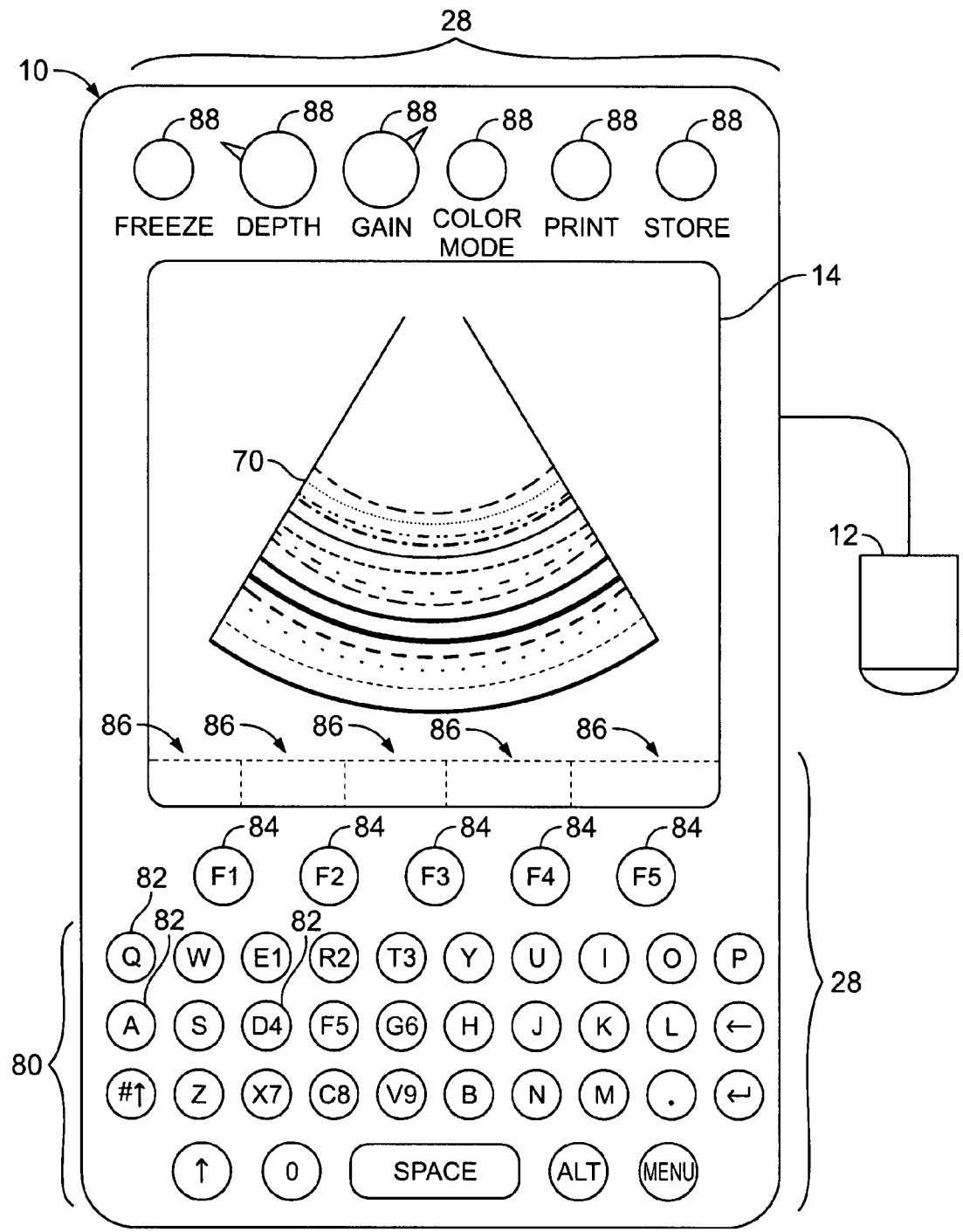
FIG. 3 is a pictorial drawing of an embodiment of a hand carried medical imaging device of the present invention.

FIG. 3 is a pictorial drawing of an embodiment of a hand carried medical imaging device 10 of the present invention. Hand carried medical imaging device 10 includes the display 14, for example, a 320×320 pixel color LCD display (on which a medical image 70 may be displayed), user interface 28, and is interconnected with probe 12. A typewriter-like keyboard 80 of buttons 82 may be included in user interface 28. Multi-function controls 84 may each be assigned functions in accordance with the mode of system operation as previously discussed. As each of the multi-function controls 84 may be configured to provide a plurality of different physical actions, the mapping of system response to intuitive physical action may be improved without requiring additional space. Label display areas 86 associated with the multi-function controls 84 may be included as necessary on the display 14. The device may also have additional keys and/or controls 88 for special purpose functions, which may include, but are not limited to "freeze," "depth control," "gain control," "color-mode," "print," and "store."

Figure 4:
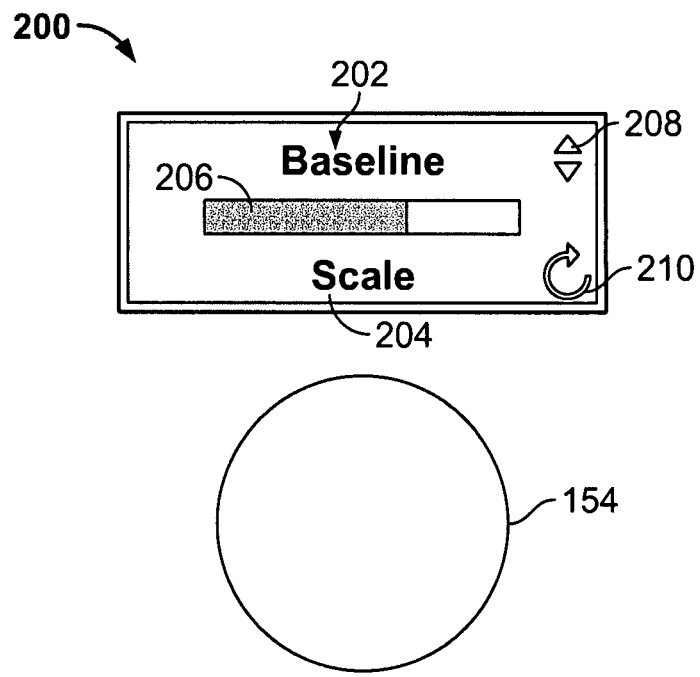
FIG. 4 illustrates a label that displays multiple system parameters that are mapped to physical actions of a multi-function control in accordance with an embodiment of the present invention.

FIG. 4 illustrates a label 200 that displays multiple system parameters that are mapped to physical actions of the first multi-function control 154. Therefore, the first multi-function control 154 may be context sensitive. The label 200 may be displayed on the display 152, such as within the first label display area 180, or on a different display (not shown) located proximate to the first multi-function control 154. The label 200 displays a system parameter proximate to a graphical indicator of a physical action. The graphical indicator indicates what manipulation the user is required to accomplish with the first multi-function control 154 to generate a system response associated with the system parameter.

For example, the label 200 indicates that the system parameters baseline 202 and scale 204 are controlled by the first multi-function control 154. However, similar functionality and operation may be provided by any of the multi-function controls. The label 200 also indicates the physical action required to change each of the system parameters. An up/down toggle indicator 208 is associated with the baseline 202 and a rotary 210 is associated with the scale 204. Therefore, within the context of the particular system state or the current application of the ultrasound system 100, the physical states currently activated on the first multi-function control 154 are up/down toggle and CW/CCW rotate. Optionally, other physical states on the first multi-function control 154 may be activated and not displayed on the label 200.

When the user wishes to change the baseline 202, the user may toggle the first multi-function control 154 in an up or down direction. The physical action is intuitive, as most users would associate up/down toggling with increasing and decreasing, respectively, a system parameter. To change the scale 204, the user may rotate the first multi-function control 154 in the CW and CCW directions to increase and decrease, respectively, the scale 204.

A gauge 206 may be used to indicate a current value relative to an allowable range of values. The gauge 206 may be updated to reflect the most recently manipulated physical control, such as displaying a current scale setting relative to a full range of the scale control as the user rotates the first multi-function control 154 to increase or decrease the scale. Optionally, the gauge 206 may be displayed in a color to indicate an association with one of the system parameters. For example, the gauge 206 and the scale 204 may be displayed in one color while the baseline 202 is displayed in a different color. Optionally, the display color of the gauge 206 may change to reflect the most recently manipulated physical control. Optionally, more than one gauge 206 may be displayed, or the gauge 206 may be configured to display more than one parameter value at a time.

Figure 5:
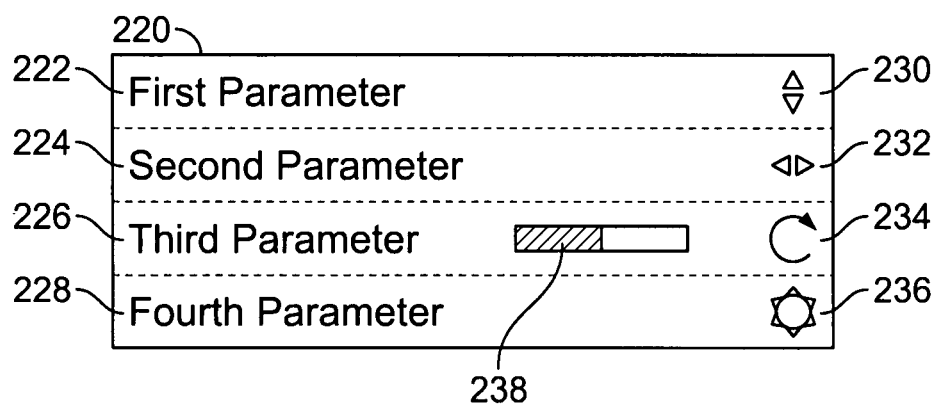
FIG. 5 illustrates a label displaying context sensitive information that is associated with a multi-function control that is configured to control numerous system parameters or functions within the given context of the ultrasound system in accordance with an embodiment of the present invention.

FIG. 5 illustrates label 220 that displays context sensitive information associated with a multi-function control (not shown) that is configured to control at least four different system parameters or functions within the given context or machine state. First, second, third and fourth parameters 222, 224, 226 and 228 are illustrated. Up/down toggle indicator 230 is associated with the first parameter 222, left/right toggle indicator 232 is associated with the second parameter 224, rotary indicator 234 is associated with the third parameter 226, and push indicator 236 is associated with the fourth parameter 228. It should be understood that the graphical indictors may be different than illustrated, and that the user may customize the system parameters, the graphical indicators that are displayed, as well as the mapping there-between. Also, the physical order and physical presentation of the system parameters and associated graphical indicators is exemplary and is not limited to those indicated in FIG. 5.

A default configuration may be used to map system parameters to particular physical actions as well as to particular multi-function controls based on predetermined intuitive physical actions. A user may wish to customize the mapping, and may map system parameters to physical actions that are intuitive to the user or group of users. Therefore, each user or group of users may map system parameters based on their preference.

The following examples provide possible mapping combinations of system parameters controlled by one multi-function control and the associated displayed information on the label 220. The combinations of system parameters are not limited to those discussed herein. By way of example only, the first parameter 222 may be Doppler baseline, and the up/down toggle indicator 230 indicates to the user to toggle the multi-function control up and down to move the Doppler baseline up and down, respectively. The second parameter 224 may steer the Doppler image, and the left/right toggle indicator 232 indicates to the user to toggle the multi-function control left and right to steer the image to the left and right, respectively. The third parameter 226 may be either brightness or gain, and the rotary indicator 234 indicates to the user to rotate the multi-function control CW to increase the brightness or gain and rotate the multi-function control CCW to decrease the brightness or gain. The fourth parameter 228 may be used to invert an image on the display 152 (FIG. 2), and the push indicator 236 indicates to the user that pushing the multi-function control will change the inverted/non-inverted state of the displayed image. Also, a gauge or scale 238 may be indicated, such as proximate to the third parameter 226.

In another example, three system parameters that may be commonly related are adjusting the Doppler baseline, adjusting the Doppler pulse repetition frequency or scale, and inverting the Doppler spectrum. The three system parameters or functions may be mapped to a single multi-function control and are displayed on the label 220 along with the associated graphical indicators. The Doppler baseline may be mapped to the up/down toggle indicator 230, the Doppler scale may be mapped to the rotary indicator 234, and the Doppler invert may be mapped to the push indicator 236. In this example, the left/right toggle physical action may not be currently mapped to a system parameter. If the user manipulates the left/right toggle, the ultrasound system 100 may ignore the physical action, display a message to the user informing them that the physical action is invalid or not mapped to a system parameter, and/or activate a sound to alert the user.

In a further example, the system parameters may be related to manipulation of a volume. The rotation of the volume about the x-axis may be mapped to the up/down toggle indicator 230, the rotation of the volume about the y-axis may be mapped to the left/right toggle indicator 232, the rotation about the z-axis may be mapped to the rotary indicator 234, and resetting the orientation of the volume may be mapped to the push indicator 236. In this case, the multi-function control has eight different states controlled by seven different physical actions, providing the ability to map intuitive physical actions to system actions.

Figure 6:
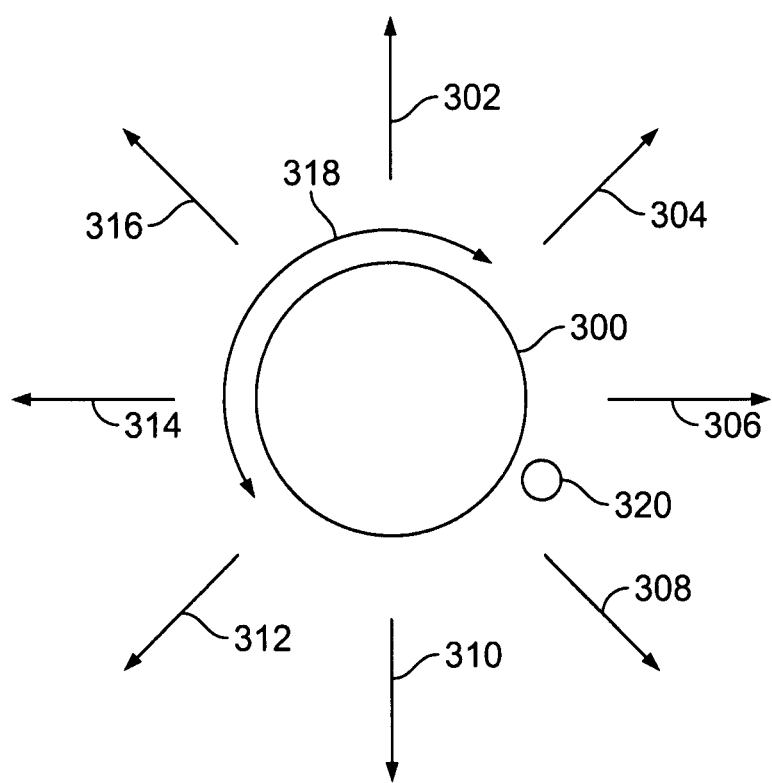
FIG. 6 illustrates a multi-function control formed in accordance with an embodiment of the present invention.

FIG. 6 illustrates a multi-function control 300 that allows the user to accomplish rotations that are not directly about an axis. The multi-function control 300 may be an eight-position joystick, for example. The multi-function control 300 may provide translational movement and be toggled in first, second, third, fourth, fifth, sixth, seventh and eighth toggle positions 302, 304, 306, 308, 310, 312, 314, and 316. Although not shown, additional toggle positions may be used. In addition, the multi-function control 300 may be rotated in CW/CCW directions, indicated by arrow 318, as well as pushed, indicated by dot 320. Therefore, the multi-function control 300 is configured to provide eleven physical actions to accomplish twelve functional states. Referring to the label 220 of FIG. 5, the second, fourth, sixth and eighth toggle positions 304, 308, 312, and 316 may be indicated with graphical indicators such as arrows aimed in appropriate directions to provide visual cues to the user.

Figure 7:
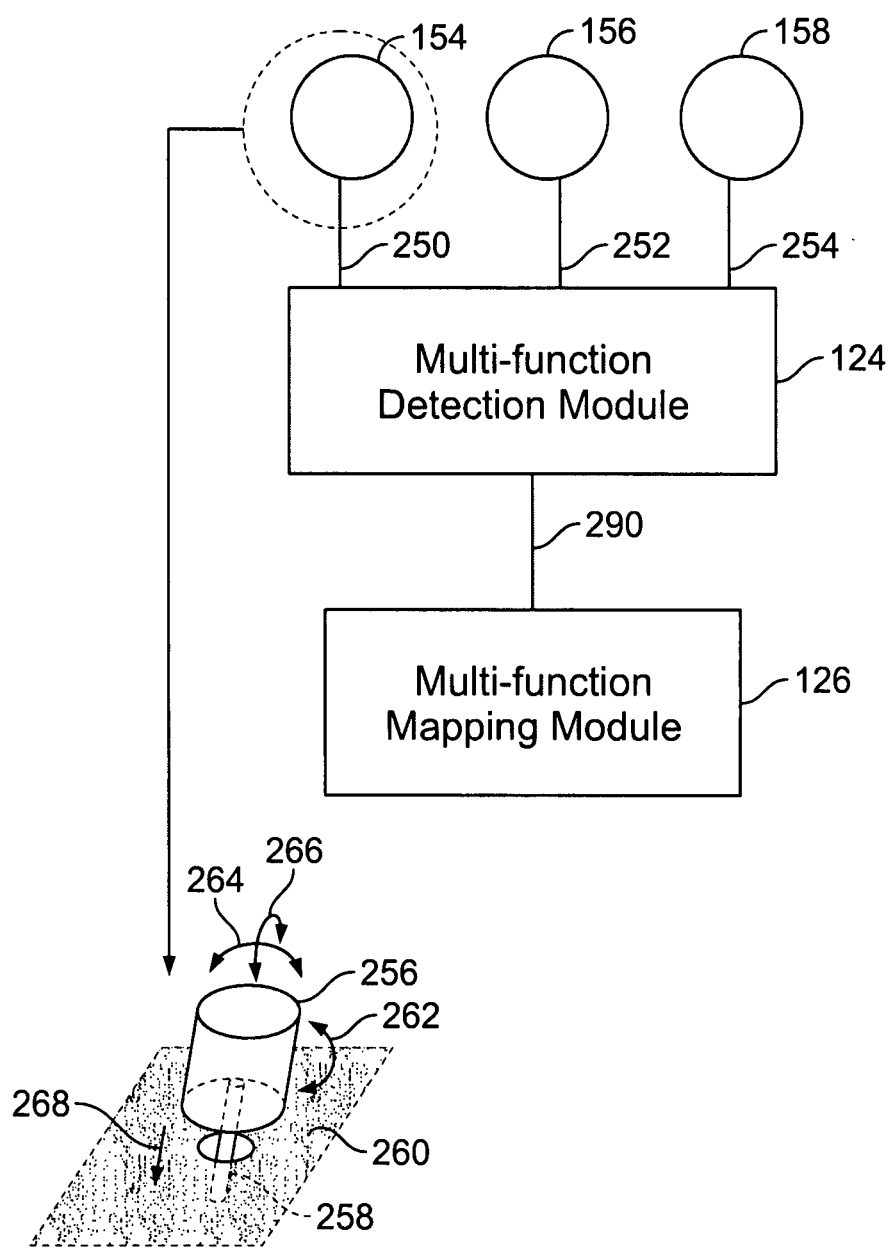
FIG. 7 illustrates a block diagram of the detection of user manipulation of a multi-function control in accordance with an embodiment of the present invention.

FIG. 7 illustrates a block diagram of the detection of user manipulation of the multi-function controls. In this example, the first, second and third multi-function controls 154, 156 and 158 provide input to the multi-function detection module 124 via lines 250, 252 and 254, respectively. Although not shown in FIG. 7, the fourth through twelfth multi-function controls 160-176 also provide input to the multi-function detection module 124.

Each of the multi-function controls may be a unit having an output connected to the associated line 250, 252 and 254. The first multi-function control 154 is illustrated in more detail, and it should be understood that other configurations and implementations of a multi-function control may be used. The first multi-function control 154 has a circular shaped rotary knob 256 mounted on a stem 258. The first multi-function control 154 may be implemented, for example, by using a rotatable joystick. The stem 258 extends above a surface 260 of the user interface 150 (as shown in FIG. 2) at one end, and interfaces with the line 250 at the other end. For example, the first multi-function control 154 may be manipulated by the user in seven physical positions, such as CW/CCW directions 262, left/right toggle directions 264, up/down toggle directions 266, and push direction 268. Alternatively, the first multi-function control 154 may be manipulated by the user in eleven physical positions as discussed with respect to the multi-function control 300 in FIG. 6.

Figure 8:
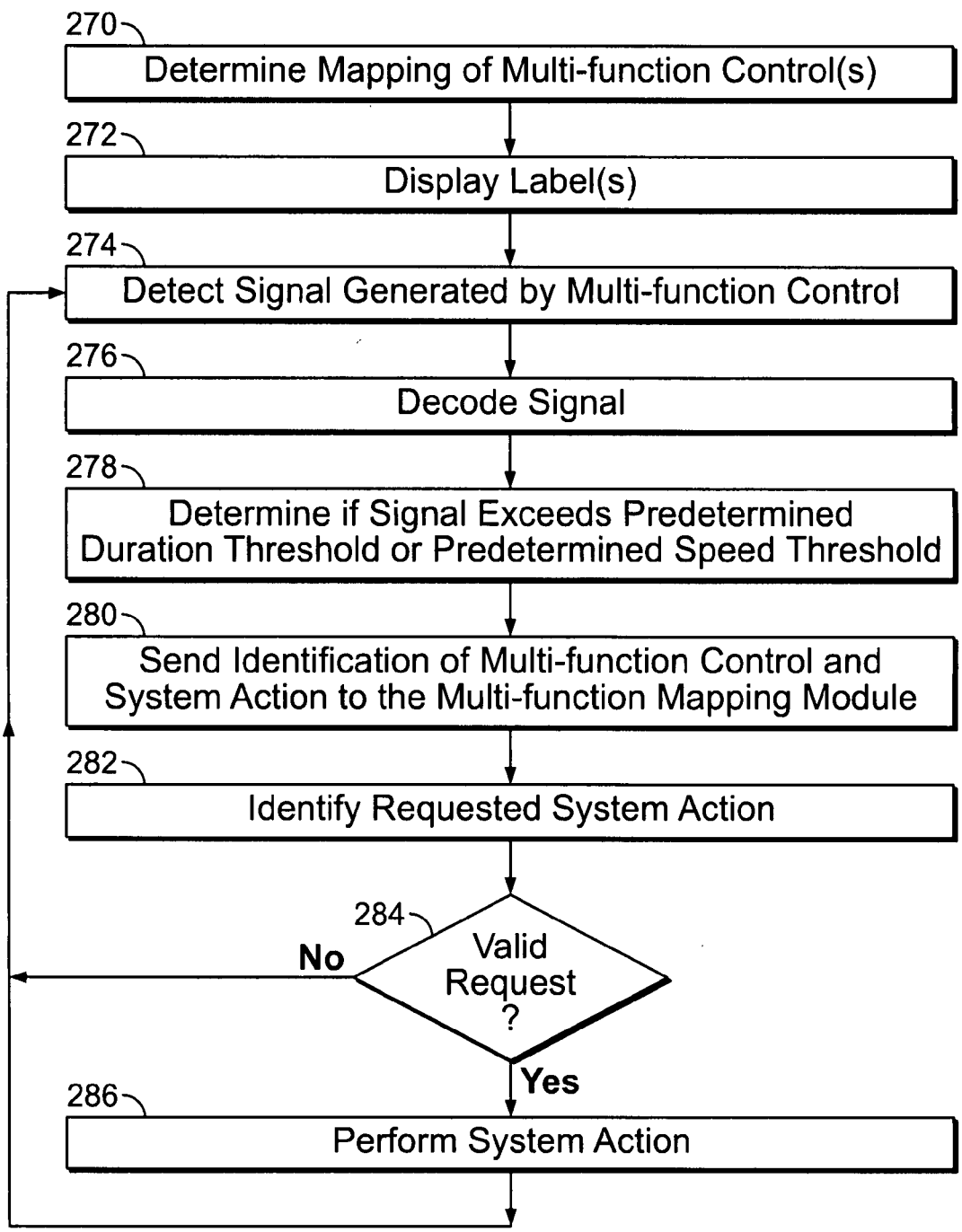
FIG. 8 illustrates a method for using the multi-function controls provided on the user interfaces of FIGS. 2 and 3 in accordance with an embodiment of the present invention.

FIG. 8 illustrates a method for using the multi-function controls provided on the user interface 150 of FIG. 2 and the user interface 28 of FIG. 3. The multi-function controls may be used during an acquisition of ultrasound data as well as during processing of previously acquired ultrasound data. FIG. 8 will be discussed in connection with FIG. 7.

At 270, the multi-function mapping module 126 determines the mapping of the first through twelfth multi-function controls 154-176. For example, the multi-function mapping module 126 determines the machine state or mode of operation of the ultrasound system 100. The machine state may correspond to a user selected protocol or by an input by the user through the user interface 150 (FIG. 2). For example, the machine state may be a particular imaging protocol such as cardiac imaging or fetal imaging, for example, wherein specific system parameters and actions are typically used. The mapping may be accomplished with a database, matrix or lookup table stored in the memory 122, or other mapping function. The multi-function mapping module 126 may use default or user defined mapping, as previously discussed. Also, not all of the first through twelfth multi-function controls 154-176 may be mapped to system parameters for each machine state.

At 272, the multi-function mapping module 126 may display one or more labels 200 and 220 (FIGS. 3 and 4) associated with particular multi-function controls. As discussed previously, the labels 200 and 220 may be displayed on the display 152 (FIG. 2) or in a separate display window proximate to the associated first through twelfth multi-function control 154-176.

At 274, the multi-function detection module 124 detects a signal from one of the first through twelfth multi-function controls 154-176. In the example of FIG. 7, multi-function detection module 124 detects signals from the first, second and third multi-function controls 154, 156 and 158 via lines 250, 252 and 254, respectively. It should be understood that the signals may be mechanical or electrical or other type of signal known in the art. Alternatively, the signals may be combined on a signal input that is provided on one line to the multi-function detection module 124, provided via a signal bus, and the like.

At 276, the multi-function detection module 124 decodes the signal to determine the physical action that was acted upon the associated multi-function control. For example, each physical action may generate a different voltage level or a different digital message identifier. Other mechanisms may be used to convey the physical action. If necessary, such as when more than one input signal is combined on a single input, the multi-function detection module 124 also decodes the signal to determine which one of the first, second and third multi-function controls 154, 156 and 158 generated the signal.

At 278, the multi-function detection module 124 determines whether the signal exceeds a predetermined duration threshold or a predetermined speed threshold. As discussed previously, the predetermined speed threshold and/or the predetermined duration threshold may be determined based on the system state, and thus may be specific to a particular application and may change from one multi-function control to the next. For example, the multi-function detection module 124 may detect multiple consecutive movements of the rotary action (CW/CCW direction 262). The multi-function detection module 124 may then determine a speed of rotation that may be compared to a predetermined speed threshold. If the speed of rotation is greater than the predetermined speed threshold, the multi-function detection module 124 may determine that the system response is to be made in greater increments. Also, if multiple consecutive detections are detected from a toggle action (left/right toggle direction 264 or up/down toggle direction 266), indicating that a toggle action is being held by the user, the multi-function mapping module 126 may compare a time duration of the toggle to the predetermined duration threshold to determine if the associated system response is to be made in greater increments and/or at a faster rate.

At 280, the multi-function detection module 124 outputs multi-function control information via line 290 to the multi-function mapping module 126. The multi-function control information identifies the multi-function control that generated the input detected at 274, the type of physical action detected at 276, as well as whether predetermined limits associated therewith have been exceeded.

At 282, the multi-function mapping module 126 may identify a system action or response that is associated with the multi-function control information. For example, the multi-function mapping module 126 may have identified a specific matrix associated with the system state identified at 270, to which the multi-function control information is compared. In some cases, no system action will be identified as the detected physical action of the multi-function control is not assigned to a system function during the particular system state. Therefore, at 284, if the detected action is not valid and/or has no assigned system function, the method returns to 274 to wait for the next input signal from a multi-function control. Optionally, a message or other indication may be produced to notify the user of the invalid action, as discussed previously. If the request is valid, then at 286 the ultrasound system 100 performs the requested system action. A system response may be an adjustment of an image parameter on the display 152, such as a change in baseline, brightness, or contrast, a change in acquisition scanning parameters, displaying a different type of image or an additional image, or any other system request that has been mapped to the physical action of the multi-function control. The method then returns to 274.

A technical effect of various embodiments of the present invention is the use of multi-function controls that have multiple physical states. All or some physical actions, such as CW/CCW rotation, pushbutton selection, and toggling in two or more directions may be provided on a single multi-function control. The multi-function controls may be context sensitive, and thus may be mapped to provide an intuitive user interface based on the current machine state of the ultrasound system and/or user preferences. Labels may be provided proximate to the multi-function controls to provide action information to the user. By combining multiple functions on one multi-function control, intuitive control is enhanced and the amount of space needed is minimized, contributing to the overall minimization of the size of the user interface.

While the invention has been described in terms of various specific embodiments, those skilled in the art will recognize that the invention can be practiced with modification within the spirit and scope of the claims.

What is claimed is:

1. A user interface for controlling an ultrasound system, comprising:
a display for displaying ultrasound data;
at least one multi-function control configured to control different functions of the ultrasound system, the multi-function control having a corresponding user operable member configured to extend above a surface of the ultrasound system, at least one of the user operable members being movable with physical actions comprising both rotational and translational movements, wherein the movements are associated with different system parameters corresponding to different ultrasound system actions; and
a label being displayed on the display, the label being associated with the multi-function control, wherein the label comprises a plurality of defined parameters and graphical indicators associated with the physical actions of the multi-function control.

2. The user interface of claim 1, wherein the physical actions further comprise a push movement.

3. The user interface of claim 1, wherein the rotational movement further comprises clockwise rotation and counter-clockwise rotation.

4. The user interface of claim 1, wherein the user operable member being a rotatable joystick.

5. The user interface of claim 1, wherein the translational movement further comprises a toggling movement in first and second directions.

6. The user interface of claim 1, wherein the translational movement further comprises a toggling movement in at least four directions that are different with respect to each other.

7. The user interface of claim 1, further comprising context sensitive information being displayed on the display as part of the label and associated with the multi-function controls, the context sensitive information identifying a plurality of defined parameters controllable by the multi-function control, and wherein a plurality of graphical indicators associate different ones of the physical actions with different defined parameters.

8. The user interface of claim 1, further comprising a multi-function mapping module configured to identify a machine state of the ultrasound machine, the multi-function mapping module further configured to identify the multiple functions associated with the multi-function control based on the machine state.

9. The user interface of claim 1, further comprising a plurality of multi-function controls, wherein at least a portion of the plurality of multi-function controls are positioned proximate each other to minimize movement of a user's hand.

10. The user interface of claim 1, wherein the parameters and associated physical actions are pre-assigned.

11. A method for controlling an ultrasound system, comprising:
detecting a physical action that physically moves at least a portion of a multi-function control configured to allow both translational and rotational movements, the physical action being one of at least four physical actions of the user operable members, wherein the physical actions of the multi-function control are associated with different system actions;
mapping system parameters to the four physical actions of the multi-function control;
displaying a label associated with the multi-function control, the label displaying a plurality of different graphical indicators associated with the four physical actions, the label further displaying a system parameter associated with each of the physical actions; and
performing a system action associated with the physical action, wherein first and second system actions associated with first and second physical actions from the four physical actions of the multi-function control are different with respect to each other;
detecting one of the first and second physical actions that physically moves at least a portion of another multi-function control; and
performing a third system action associated with the one of the first and second physical actions, wherein the third system action is different with respect to the first and second system actions.

12. The method of claim 11, further comprising detecting a third physical action of the multi-function control from the four physical actions, the third physical action being a translational movement in one of eight directions, the eight directions being different with respect to each other.

13. The method of claim 12, further comprising:
mapping system parameters to the second and third physical actions of the multi-function control; and
displaying graphical indicators within the label, the graphical indicators being associated with the second and third physical actions.

14. The method of claim 11, further comprising detecting a third physical action of the multi-function control from the four physical actions, wherein the third physical action is a push movement that physically moves at least a portion of the multi-function control.

15. The method of claim 11, further comprising:
determining a speed of rotation associated with the first physical action; and
modifying the first system action when the speed of rotation is greater than a predetermined speed threshold.

16. The method of claim 11, further comprising:
determining a duration of time associated with the second physical action; and
modifying the second system action when the duration of time is greater than a predetermined duration threshold.

17. The method of claim 11, further comprising:
detecting a mode of operation of the ultrasound system; and
mapping first and second system parameters to the first and second physical actions, the system parameters being based on the mode of operation.

18. A method for controlling an ultrasound system, comprising:
detecting a machine state of an ultrasound system;
detecting a physical action that physically moves a user operable member of a multi-function control interconnected with the ultrasound system, the multi-function control configured to allow both translational and rotational movements, the physical action being one of at least four physical actions of the user operable members, wherein the physical actions of the multi-function control are associated with different system actions;

displaying a label associated with the multi-function control, the label displaying a plurality of different graphical indicators associated with the four physical actions, the label further displaying a system parameter associated with each of the physical actions; and performing the system action that is associated with the physical action, the multi-function control, and the machine state.

19. The method of claim 18, further comprising displaying a label associated with one of the at least two multi-function controls, the label displaying at least one unique graphical indicator that is associated with one of the physical actions.

20. The method of claim 18, the method further comprising displaying a label associated with one of the at least two multi-function controls, the label displaying at least one of a first graphical indicator associated with a rotational movement, a second graphical indicator associated with a push movement, a third graphical indicator associated with a toggling movement in first and second directions, and a fourth graphical indicator associated with a toggling movement in third and fourth directions, the first, second, third and fourth graphical indicators being different from each other.

21. A user interface for controlling an ultrasound system, comprising:

a display for displaying ultrasound data; and at least one multi-function control configured to control different functions of the ultrasound system, the multi-function control having a corresponding user operable member configured to extend above a surface of the ultrasound system, at least one of the user operable members being movable with physical actions comprising both rotational and translational movements, wherein the movements are associated with different system parameters corresponding to different ultrasound system actions, and a plurality of labels each having a defined set of parameters controllable by the multi-function control and associated graphical indicators associating the rotational and translational movements to the parameters, wherein a label from the plurality of labels is displayed based on a mode of operation.

22. The user interface of claim 21, wherein at least one of the graphical indicators is not displayed in one of the modes of operation corresponding to a physical action not used in the mode of operation.

23. The user interface of claim 21, wherein at least one of the physical actions controlling the defined parameters is different for different modes of operation.

* * * * *